(12) United States Patent
Therre et al.

(10) Patent No.: US 8,574,873 B2
(45) Date of Patent: Nov. 5, 2013

(54) PROCESS FOR THE PREPARATION OF HOMOPOLYSACCHARIDES

(75) Inventors: Jörg Therre, Worms (DE); Hartwig Voβ, Frankenthal (DE); Julia Kristiane Schmidt, Heidelberg (DE); Tillmann Faust, Weisenheim am Sand (DE); Rajan Hollmann, Bad Essen (DE)

(73) Assignee: Wintershall Holding GmbH (DE)

( * ) Notice: Subject to any disclaimer, the term of this patent is extended or adjusted under 35 U.S.C. 154(b) by 133 days.

(21) Appl. No.: 12/967,099

(22) Filed: Dec. 14, 2010

(65) Prior Publication Data

US 2011/0151517 A1 Jun. 23, 2011

Related U.S. Application Data

(60) Provisional application No. 61/287,224, filed on Dec. 17, 2009.

(30) Foreign Application Priority Data

Dec. 17, 2009 (EP) .................................... 09179716

(51) Int. Cl.
C12N 9/24 (2006.01)
(52) U.S. Cl.
USPC ............................ 435/74; 435/41; 435/295.3
(58) Field of Classification Search
USPC .......................................... 435/41, 74, 295.3
See application file for complete search history.

(56) References Cited

U.S. PATENT DOCUMENTS

2011/0009645 A1  1/2011  Birnbach et al.

FOREIGN PATENT DOCUMENTS

| CA | 2063490 A1 | 9/1992 |
|---|---|---|
| CA | 13259159 C | 5/1994 |
| DE | 4012238 A1 | 1/1991 |
| EP | 271907 A2 | 6/1988 |
| EP | 504673 A1 | 9/1992 |
| WO | WO-03/016545 A2 | 2/2003 |
| WO | WO2009/106605 A1 | 9/2009 |
| WO | WO2010/000719 A1 | 1/2010 |
| WO | WO2010/018075 A1 | 2/2010 |
| WO | WO2010/037690 A1 | 4/2010 |
| WO | WO2010/076251 A1 | 7/2010 |
| WO | WO2010/092155 A1 | 8/2010 |
| WO | WO2010/125025 A1 | 11/2010 |

OTHER PUBLICATIONS

Rau, Udo. Carbohydrate Biotechnology Protocols. Methods in Biotechnology. 1999, vol. (10); pp. 43-55.*
Millipore. Maintenance Guide for Tangential Flow Filters and Systems. Millipore Technical Publications. 1989, pp. 1-24.*
PALL Corporation. Pall Membralox® Ceramic Membranes and Modules. Jul. 2007. pp. 1-2.*
Bruggen, Bart et al. A Review of Pressure-Driven Membrane Processes in Wastewater Treatment and Drinking Water Production. Environmental Progress. Apr. 2003. vol. 22 (1): pp. 46-56.*
Rau, U., "Biosynthese, Produktion und Eigenschaften von extrazellulären Pilz-Glucanen", *Habilitationsschrift*, Technical University of Brunswick, (1997), pp. 70-95.
Rau, U., *Biopolymers*, Editor A. Steinbüchel, Wiley-VCH Publishers, New York, vol. 6, (2002), pp. 63-79.
Rau, U., et al., "Process Included Downstream Processing of Branched β-1,3-Glucans (Schizophyllan)", *GIT Fachzeitung Labor* Dec. 1992, pp. 1233-1238.
Melin, T. and Rautenbach, R., *Membranverfahren*, Springer-Verlag, 3$^{rd}$ Ed. (2007), pp. 51-52 and 309-366.

* cited by examiner

*Primary Examiner* — Susan Hanley
*Assistant Examiner* — Nghi Nguyen
(74) *Attorney, Agent, or Firm* — Novak Druce Connolly Bove + Quigg LLP

(57) ABSTRACT

A process for the preparation of aqueous solutions of glucans having a β-1,3-glycosidically-linked main chain and side groups having a β-1,6-glycosidic bond by fermentation of fungal strains. The fungal strains secrete the glucans into the fermentation broth, in an aqueous culture medium, and the separation of the glucans from the fermentation broth is effected using asymmetrical filter membranes.

11 Claims, 3 Drawing Sheets

PROCESS FOR THE PREPARATION OF HOMOPOLYSACCHARIDES

RELATED APPLICATIONS

This application claims the benefit of U.S. Provisional Application No. 61/287,224, filed Dec. 17, 2009, and the priority of EP 09179716.7, filed Dec. 17, 2009, both of which are incorporated herein by reference.

BACKGROUND OF THE INVENTION

The present invention relates to a process for the preparation of aqueous solutions of glucans having a β-1,3-glycosidically linked main chain and side groups having a β-1,6-glycosidic bond thereto by fermentation of fungal strains, which secrete said glucans into the fermentation broth, in an aqueous culture medium, the separation of the glucans from the fermentation broth being effected with the use of asymmetrical filter membranes.

In natural mineral oil deposits, mineral oil is present in the cavities of porous reservoir rocks which are closed off from the earth's surface by impermeable covering layers. The cavities may be very fine cavities, capillaries, pores or the like. Fine pore necks can have, for example, a diameter of only about 1 μm. In addition to mineral oil, including natural gas fractions, the deposits comprise water having a higher or lower salt content.

In mineral oil production, a distinction is made between primary, secondary and tertiary production.

In primary production, after sinking of the well into the deposit, the mineral oil flows by itself through the well to the surface owing to the autogenous pressure of the deposit. However, in general only from about 5 to 10% of the amount of mineral oil present in the deposit, depending on the type of deposit, can be extracted by means of primary production, after which the autogenous pressure is no longer sufficient for extraction.

Secondary production is therefore used after the primary production. In secondary production, further wells are drilled into the mineral oil-carrying formation, in addition to the wells which serve for production of the mineral oil, the so-called production wells. Water and/or steam is forced into the deposit through these so-called injection wells in order to maintain or to increase again the pressure. By forcing in the water, the mineral oil is forced slowly through the cavities in the formation, starting from the injection well, in the direction of the production well. However, this functions only as long as the cavities are completely filled with oil and the water pushes the more viscous oil in front of it. As soon as the low-viscosity water penetrates through cavities, it flows from this time on along the path of least resistance, i.e. through the resulting channel between the injection wells and the production wells, and no longer pushes the oil in front of it. As a rule, only from about 30 to 35% of the amount of mineral oil present in the deposit can be extracted by means of primary and secondary production.

It is known that the mineral oil yield can be further increased by tertiary oil production measures. Tertiary mineral oil production includes processes in which suitable chemicals are used as assistants for oil production. These include the so-called "polymer flooding". In polymer flooding, an aqueous solution of a polymer having a thickening effect is forced instead of water through the injection wells into the mineral oil deposit. By forcing in the polymer solution, the mineral oil is forced through said cavities in the formation, starting from the injection well, in the direction of the production well, and the mineral oil is finally extracted via the production well. Owing to the high viscosity of the polymer solution, which is adapted to the viscosity of the mineral oil, the polymer solution can no longer, or at least not so easily, break through cavities as is the case with pure water.

A multiplicity of different water-soluble polymers have been proposed for polymer flooding, i.e. both synthetic polymers, such as, for example, polyacrylamides or copolymers comprising acrylamide and other monomers and also water-soluble polymers of natural origin.

Suitable thickening polymers for tertiary mineral oil production must meet a number of specific requirements. In addition to sufficient viscosity, the polymers must also be thermally very stable and retain their thickening effect even at high salt concentrations.

An important class of polymers of natural origin for polymer flooding comprises branched homopolysaccharides obtained from glucose. Polysaccharides comprising glucose units are also referred to as glucans. Said branched homopolysaccharides have a main chain of β-1,3-linked glucose units, of which—in statistical terms—about every third unit has a β-1,6-glycosidic linkage to a further glucose unit. Aqueous solutions of such branched homopolysaccharides have advantageous physicochemical properties, so that they are particularly suitable for polymer flooding.

Homopolysaccharides of said structure are secreted by various fungal strains, for example by the Basidiomycetes *Schizophyllum commune*, which exhibits filamentous growth and, during the growth, secretes homopolysaccharide of said structure having a typical molecular weight $M_w$ of from about 5 to about $25 \cdot 10^6$ g/mol (trivial name schizophyllan). Homopolysaccharides of said structure which are secreted by *Sclerotium rolfsii* may furthermore be mentioned (trivial name: scleroglucans).

It is important for polymer flooding that the aqueous polymer solution used for this purpose comprises no gel particles or other small particles at all. Even a small number of particles having dimensions in the micron range may block the fine pores in the mineral oil formation and thus at least complicate or even stop the mineral oil production. Polymers for tertiary mineral oil production should therefore have as small a proportion as possible of gel particles or other small particles.

For use for polymer flooding, it is therefore important that solutions of said homopolysaccharides are substantially free of cells and cell fragments, since these otherwise block the mineral oil formation, which complicates the extraction of the mineral oil or even makes it impossible. The so-called Millipore Filtration Ratio (MPFR value) can be used as a characteristic for a good quality of a polymer solution. The way in which the filter resistance changes in the course of time during filtering of a solution is determined here.

DESCRIPTION OF RELATED ART

Processes for the preparation of branched homopolysaccharides comprising β-1,3-linked glucose units are known.

EP 271 907 A2, EP 504 673 A1 and DE 40 12 238 A1 disclose processes for the preparation, i.e. the preparation is effected by batchwise fermentation of the fungus *Schizophyllum commune* with stirring and aeration. The culture medium substantially comprises glucose, yeast extract, potassium dihydrogen phosphate, magnesium sulfate and water. EP 271 907 A2 describes a method for isolating the polysaccharide, in which the culture suspension is first centrifuged and the polysaccharide is precipitated from the supernatant with isopropanol. A second method comprises a pressure filtration followed by an ultrafiltration of the solution obtained, without details of the method having been disclosed.

"Udo Rau, *"Biosynthese, Produktion and Eigenschaften von extrazellulären Pilz-Glucanen"*, Habilitationsschrift, Technical University of Brunswick, 1997, pages 70 to 95", describes the preparation of schizophyllan by continuous or batchwise fermentation. The schizophyllan can be separated off by means of crossflow filtration (loc. cit., page 75). For separating off the cell mass, various stainless steel membranes having pore diameters of 0.5 µm, 2 µm, 10 µm and 20 µm were tested. With 2 µm membranes, however, only small permeation rates were obtained with a solution which comprised 0.5 g/l of glucan and 0.5 g/l of dry biomass. Moreover, hypha fragments in a concentration of about 0.1 g/ml remained. A second ultrafine clarification step is therefore proposed (loc. cit., page 94). Such a process is very complicated and moreover stainless steel membranes are very expensive.

"Udo Rau, *Biopolymers*, Editor A. Steinbüchel, Volume 6, pages 63 to 79, WILEY-VCH Publishers, New York, 2002" describes the preparation of schizophyllan by continuous or batchwise fermentation. Centrifuging and crossflow microfiltration are recommended for recovering the cell- and cell fragment-free schizophyllan (loc. cit., page 78, section 10.1). For the crossflow microfiltration, the use of sintered stainless steel membranes having a pore size of 10 µm is proposed there. The permeate thus obtained must, however, be purified again by means of diafiltration and, if necessary, be further purified by means of crossflow microfiltration (loc. cit., page 78, section 10.2). Such a process is very complicated and moreover stainless steel membranes are very expensive.

"GIT Fachzeitung Labor 12/92, pages 1233-1238" describes a continuous preparation of branched β-1,3-glucans with cell recycling. First, a crossflow filtration by means of stainless steel membranes which have a pore size of 200 µm is proposed for separating the branched β-1,3-glucans from the fermentation circulation. The polymer-containing permeate obtained is, however, still contaminated with large amounts of cell fragments and must be subsequently purified in a second step. A deep-bed filtration using a glass fiber deep-bed filter, a three-stage pressure filtration and centrifuging are proposed for this purpose. As a further method for the second purification stage, the authors have unsuccessfully investigated crossflow filtration of the ceramic membranes. As a result of their experiments, they draw the conclusion that crossflow microfiltration is not suitable for cell separation of mycelium-containing, high-viscosity culture suspensions. The permeate obtained is finally subsequently purified in a third purification stage by means of diafiltration. Such a three-stage process is, however, very complicated and accordingly unsuitable for an industrial production process.

WO 03/016545 A2 discloses a continuous process for the preparation of scleroglucans using *Sclerotium rolfsii*. For purification, a crossflow filtration using stainless steel filters having a pore size of 20 µm with a transmembrane flow velocity of at least 7 m/s is described. However, a 20 µm filter is not sufficient for separating off very small particles.

It is true that in principle the removal of fine particles could be improved by the use of finer filter membranes. With decreasing pore size, however, the filter membranes increasingly also retain the glucans in an undesired manner, in particular the fractions having very high molecular weights. Furthermore, finer membranes require higher filter pressures and the danger that the fungus could be subjected to an excess of mechanical load therefore increases. It is intended to avoid destruction and lysis of cells, because the polymer to be prepared will be contaminated thereby.

Furthermore, for economic reasons, the concentration of aqueous glucan solutions obtained should be as high as possible, i.e. firstly to be able to use as small fermentation plants as possible and secondly to ensure as little transport effort as possible for transporting the aqueous glucan solutions from the production site to the place of use. For economic reasons, a concentration of at least 3 g/l of glucan should be strived for. Glucan solutions having such a high concentration have very high viscosity and moreover have a high structural viscosity. Such solutions are difficult to filter. The higher the concentration, the more difficult is the filtration step.

BRIEF SUMMARY OF THE INVENTION

It was an object of the present invention to provide an economical process for the preparation of solutions of branched β-1,3-glucans, where the solutions should have the quality sufficient for use in tertiary mineral oil production. In addition to a high specific viscosity, the solutions should in particular have as low a content of cells and cell fragments as possible. With the filtrates, filterability specification values MPFR<2.5 should be achieved with 1.2 µm Isopore filters.

Accordingly, a process for the preparation of aqueous solutions of glucans having a β-1,3-glycosidically linked main chain and side groups having a β-1,6-glycosidic bond thereto was found, the process comprising the fermentation of fungal strains, which secrete glucans of said structure, in an aqueous culture medium, and subsequent separation of an aqueous solution of the resulting glucan from the aqueous fermentation broth comprising glucans and biomass by crossflow microfiltration, asymmetrical filter membranes comprising at least one layer of a support material and at least one separating layer being used for the crossflow microfiltration, the pore size of the separating layer being from 1 µm to 10 µm and the pore size of the support material being from 5 µm to 100 µm, with the proviso that the pore size of the separating layer is at least 1 µm greater than the pore size of the support material, and the flow velocity of the crossflow being from 0.2 m/s to 20 m/s and the transmembrane pressure being from 0.1 to 10 bar.

DETAILED DESCRIPTION OF THE INVENTION

Figure 1:
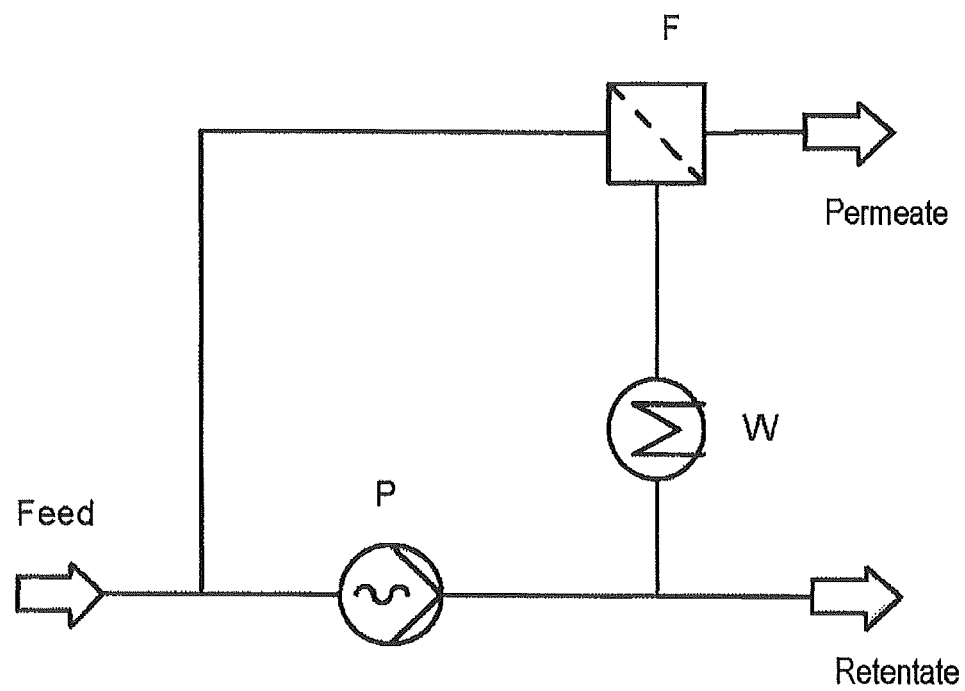
FIG. 1: schematic diagram of a preferred filtration apparatus

Regarding the invention, the following may be stated specifically:

"Glucans" is understood by the person skilled in the art as meaning homopolysaccharides which are composed exclusively of glucose units. By means of the process according to the invention, a specific class of glucans is prepared, and in particular those which comprise a main chain of β-1,3-glycosically linked glucose units and side groups having a β-1,6-glycosidic bond thereto and comprising glucose units. Preferably, the side groups consist of a single β-1,6-glycosically bonded glucose unit, where—in statistical terms—every third unit of the main chain has a β-1,6-glycosidic linkage to a further glucose unit.

Such fungal strains secreting glucans are known to the person skilled in the art. Examples comprise *Schizophyllum commune, Sclerotium rolfsii, Sclerotium glucanicum*,

*Monilinia fructigena, Lentinula edodes* or *Botlytis cinera*. Suitable fungal strains are furthermore mentioned, for example, in EP 271 907 A2 and EP 504 673 A1, in each case in claim 1. Preferably, the fungal strains used are *Schizophyllum commune* or *Sclerotium rolfsii* and particularly preferably *Schizophyllum commune*, which secretes a glucan in which, on a main chain comprising β-1,3-glycosidically linked glucose units, in statistical terms, every third unit of the main chain has a β-1,6-glycosidic linkage to a further glucose unit; i.e. the glucan is preferably the so-called schizophyllan. Typical schizophyllans have a weight average molecular weight $M_w$ of from about 5 to about $25 \cdot 10^6$ g/mol.

In a first process step, the fungi are fermented in a suitable aqueous culture medium. In the course of the fermentation, the fungi secrete the abovementioned class of glucans in the aqueous fermentation broth.

Processes for the fermentation of such fungal strains are known in principle to the person skilled in the art, for example from EP 271 907 A2, EP 504 673 A1, DE 40 12 238 A1, WO 03/016545 A2 and "Udo Rau, *"Biosynthese, Produktion and Eigenschaften von extrazellulären Pilz-Glucanen"*, Habilitationsschrift, Technical University of Brunswick, 1997", which in each case also mention suitable culture media.

According to the invention, the fungi can be cultured, for example, in an aqueous culture medium at a temperature of from 15° C. to 40° C., preferably from 25 to 30° C. and, for example, at about 27° C., preferably with aeration and movement, for example using a stirrer.

In the process according to the invention, the fermentation should preferably be run in such a way that the concentration of the glucans to be prepared is at least 3 g/l in the fermentation broth to be filtered. The upper limit is in principle not limited. It depends on the viscosity which can still be handled by the fermentation apparatus used in each case.

Finally, an aqueous solution comprising glucans is separated by crossflow microfiltration from the fermentation broth which comprises dissolved glucans and biomass (fungal cells with or without cell constituents), an aqueous fermentation broth in which the biomass has a higher concentration than beforehand remaining.

In an embodiment of the process, the fermentation is carried out in a fermentation container and the content of the fermentation tank after the fermentation is filtered according to the invention with the use of asymmetrical filter membranes.

In a further embodiment of the invention, the fermentation is carried out in a suitable plant which comprises at least one fermentation container. Fermentation broth is removed continuously or from time to time from the plant via a side stream and an aqueous solution comprising glucans is separated off therefrom by crossflow microfiltration. The remaining aqueous fermentation broth in which the biomass has a higher concentration than beforehand can be at least partly recycled to the fermentation container.

The crossflow microfiltration process is known in principle to the person skilled in the art and is described, for example, in *"Melin, Rautenbach, Membranverfahren, Springer-Verlag*, 3rd edition, 2007, page 309 to page 366". Here, "microfiltration" is understood by the person skilled in the art as meaning the removal of particles having a size of from about 0.1 μm to about 10 μm.

In the crossflow filtration, a stream of the liquid to be filtered is applied, for example, by a suitable circulation pump, parallel to the surface of the membrane used as filtration material. A liquid stream therefore continuously flow over the filter membrane, and the formation of deposits on the membrane surface is prevented or at least reduced thereby. In principle, all types of pump are suitable as the pump. Owing to the high viscosity of the medium to be transported, however, in particular positive displacement pumps and very particularly eccentric screw pumps and rotary piston pumps have proven useful.

According to the invention, asymmetrical filter membranes are used for the crossflow microfiltration. Asymmetrical filter membranes consist of at least two different layers having different pore size, i.e. of at least one support layer and one separating layer. The support layer is comparatively thick and has comparatively large pores. It imparts the mechanical strength to the filter membrane. At least one separating layer having finer pores than the pores of the support layer is applied to the support layer. For example, mercury porosimetry can be used in a manner known in principle for measuring the pore sizes. Optionally, one or more intermediate layers may also be arranged between the separating layer and the support layer.

The asymmetrical membranes may be, for example, metallic membranes or ceramic membranes. The asymmetrical membranes used are preferably asymmetrical ceramic membranes. Details of asymmetrical ceramic membranes are described, for example, in *"Melin, Rautenbach, Membranverfahren, Springer-Verlag,* 3rd edition, 2007, page 51 to page 52".

The body of the ceramic or metallic membrane is produced from the support material. Suitable forms of these membrane bodies are known to the person skilled in the art and are chosen by the person skilled in the art according to the design of the filter apparatus. They may be formed, for example, as a flat membrane or tubular membrane. Flat membranes are disk-like structures. Tubular membranes are tubular structures which have a channel (single-channel membrane) or a plurality of channels (multichannel membrane). The internal diameter of the channels of tubular membranes is as a rule from 1 mm to 25 mm, in particular from 2 mm to 12.5 mm. The channels need not be round, but irregular shapes, such as, for example, polygons having rounded apices, are also possible. The tubular membranes are as a rule from 0.1 m to 5 m long, preferably from 0.5 to 2 m. Tubular membranes from 1 m to 1.2 m in length are commercially available. It is also possible for a plurality of tubular membranes to be arranged one behind the other or parallel to one another, optionally also in different housings, so-called membrane modules.

In the case of ceramic filter membranes, the support material consists of a porous inorganic material, such as, for example, alumina, silica, silicon carbide, zirconium oxide, titanium oxide or mixtures of these substances. In the case of metallic membranes, sintered metal, such as, for example, stainless steel, Hastelloy, Inconell or titanium, is used as support material. Material combinations, for example, of sintered metal supports and ceramic separating layers, are also possible. In the case of single-channel membranes or flat membranes, the support material is as a rule from 0.05 to 10 mm thick, preferably from 1 mm to 5 mm.

The use of multichannel membranes is particularly preferred. In the case of multichannel membranes, the support material forms a molding, for example, a round or hexagonal mold, into which the abovementioned channels are led. The external diameter of such a molding for multichannel membranes is as a rule from 5 mm to 100 mm, preferably from 10 mm to 50 mm.

In the process according to the invention for the preparation of glucans having a β-1,3-glycosidically linked main chain and side groups having a β-1,6-glycosidic bond thereto solution, the pore size of the support material is from 5 μm to 100 µm, preferably from 7 µm to 100 µm and particularly preferably from 10 µm to 60 µm.

Said values are in each case the pore size D90. The term "pore size D90" is known to the person skilled in the art. It is determined from a pore size distribution curve of the support material, the "pore size D90" being that pore size at which 90% of the pore volume of the material have a pore size pore size≤D90. The pore size distribution of a material can be determined, for example, by means of mercury porosimetry and/or gas adsorption methods. These methods are known in principle to the person skilled in the art and are described, for example, in the relevant standards ISO 15901-1 EN, ISO 15901-2 EN and ISO 15901-3 EN.

Optionally, one or more intermediate layers may be applied to the support material. The support layer or optionally present intermediate layers is or are followed by a separating layer. The average pore size of the separating layer is from 1 to 10 µm, preferably from 1 µm to 6 µm and particularly preferably from 2 µm to 5 µm. The values are, as described above, D90 pore sizes.

The pore sizes of the support layer and of the separating layer are chosen in each case by the person skilled in the art so that the pore size of the support layer is at least 1 µm greater than that of the separating layer. Preferably, the pore size of the support layer is at least 5 µm greater than that of the separating layer, particularly preferably at least 10 µm and, for example, at least 20 µm.

The separating layer and the intermediate layers may consist, for example, of alumina, silica, silicon carbide, zirconium oxide, titanium oxide, mixtures of these substances or metal alloys. It is not necessary for the separating layer, the intermediate layers and the support material to be produced from the same substances; often, precisely the combination of different substances is advantageous.

The thickness of the optionally present intermediate layers is from 1 µm to 500 µm. The average thickness of the separating layer is as a rule from 1 µm to 50 µm, preferably from 5 µm to 200 µm. The intermediate layers have pore sizes which are between the respectively chosen pore size of the support material and the pore size of the separating layer.

For carrying out the process according to the invention, the asymmetrical filter membranes are installed in suitable filter apparatuses. Designs of suitable filter apparatuses are known in principle to the person skilled in the art. It is advantageous if the separating layer is present between support material and retentate space, without the invention being limited thereto.

Preferably, tubular membranes can be used for carrying out the process according to the invention. In the case of tubular membranes, the retentate is preferably passed through the interior of the channel or of the channels, and the permeate accordingly emerges outward through the walls of the support material into the permeate space. It is less preferable if retentate is present outside the channel or the channels and the permeate collects in the interior of the channel or the channels.

The tubular membranes can be used as so-called monochannel elements. However, the use of multichannel elements is preferred. These elements have the advantage of the larger membrane area in combination with the same space requirement, simpler installation and hence substantially lower capital costs. In the case of these membrane elements, however, the permeate must penetrate the total support body in order to emerge from the membrane element. In the case of substances having structural viscosity, the viscosity is particularly high at low flow velocities, which makes the passage of a glucan solution through the support body more difficult. It was therefore to be presumed that, owing to the long path and the more complicated flow of the permeate through the support body, multichannel elements could not be suitable for the filtration of schizophyllan solutions.

However, it was found that, in spite of the high viscosity and structural viscosity property of the permeate, the use of multichannel elements is possible and high permeate flows can be achieved even at low transmembrane pressures.

According to the invention, the flow velocity of the crossflow should be from 0.2 m/s to 20 m/s, preferably from 0.5 m/s to 7 m/s and particularly preferably from 1 m/s to 6 m/s. A flow velocity which is too low is disadvantageous since the membrane then rapidly becomes blocked; owing the large amount of retentate to be circulated, a flow velocity which is too high gives rise to unnecessarily high costs.

The transmembrane pressure is as a rule from 0.1 bar to 10 bar, preferably from 0.5 bar to 6 bar and very particularly from 1 bar to 4 bar.

The temperature at which the crossflow microfiltration is carried out is not critical and is as a rule from 5° C. to 150° C., preferably from 10 to 80° C. and particularly preferably from 15 to 40° C. If the cells to be separated off are not to be killed, i.e. for example in processes with recycling of the biomass, the temperature should be from 15° C. to 40° C.

A preferred embodiment of a filter unit to be used according to the invention is shown in FIG. 1. The preferred apparatus comprises a circulation pump P, a filter module F and a heat exchanger W. By means of the pump P, the abovementioned crossflow of the liquid over the surface of the membrane arranged in the filter apparatus F is produced. The plant content can be thermostated by means of a heat exchanger W.

The filter apparatus F consists of a housing in which a membrane is introduced as a partition. The housing is divided by the membrane into a so-called retentate space and a permeate space. The liquid arriving from the pump P, referred to as feed, is the glucan solution, which is contaminated with the biomass. The feed enters the retentate space via at least one feed. A liquid stream, referred to as concentrate, emerges again from the retentate space through at least one discharge. The pressure in the retentate space is higher than the pressure in the permeate space. The pressure difference is referred to as transmembrane pressure. A part of the feed stream passes through the membrane and collects in the permeate space. This part of the liquid which passes through, referred to as permeate, is the glucan solution separated from biomass.

In a further embodiment of the invention, high shear forces may be obtained over the membrane surface by using rotating internals or rotating the membrane itself. In this case, the term dynamic crossflow filtration is also used. Apparatuses for carrying out a dynamic crossflow microfiltration are known to the person skilled in the art and can be acquired, for example, under the name DynaMem module from Buss-SMS-Cancler GmbH, Düren. With the use of such a dynamic crossflow microfiltration apparatus, the asymmetrical ceramic membranes described are used in disk form.

The operating time of the membrane filtration plant can optionally be prolonged by regular backwashing with permeate. For this purpose, a pressure which is higher than the pressure in the retentate space is applied at regular intervals in the permeate space and a certain amount of permeate is forced backward through the membrane into the retentate space for a defined time. This backwashing can be effected, for example, by forcing nitrogen into the permeate space, by a backwashing pump or by the use of a piston system, as sold, for example, under the name "BACKPULSE DECOLMATEUR BF 100" by Pall, Bad Kreuznach. The backwashing should be effected at intervals of from 1 minute to 5 hours, preferably at an interval of from 2 minutes to 60 minutes, without it being intended to limit the invention to this time cycle. The amount of backwashed permeate is preferably in the range from 0.05 to 5 liters per m² membrane area, but preferably in the range from 0.1 to 2 liters per m² membrane area.

Depending on the quality of the fermentation discharge used, it may be necessary to clean the filter membranes used at an appropriate time. The cleaning of the filter membranes can be effected by treating the membranes with a suitable cleaning solution at a temperature of from 20° C. to 100° C., in particular from 40° C. to 80° C. Acids (mineral acids, such as, for example, phosphoric acid, nitric acid, or organic acids, such as, for example, formic acid) can be used as cleaning solution. The acid concentration is as a rule at a concentration of from 1% by weight to 10% by weight. Better cleaning effects are achieved as a rule by the use of alkalis (e.g. sodium hydroxide solution, potassium hydroxide solution). The concentration of alkalis used is from 0.1% by weight to 20% by weight. By the addition of oxidizing substances, such as, for example, hydrogen peroxide, hypochlorite, in particular sodium hypochlorite, or peracetic acid, the cleaning effect can be substantially improved. The concentration of the oxidizing substances should be from 0.5% by weight to 10% by weight, in particular from 1% by weight to 5% by weight. The cleaning can particularly preferably be carried out with a mixture of hydrogen peroxide and alkali or hydrogen peroxide and hypochlorite. The cleaning of membranes is effected—during the plant shutdown—preferably in the state installed in the membrane filtration plant, with the aid of a cleaning-in-place system (CIP system). It has proven useful to carry out the cleaning of the filter membranes as soon as an amount of from 50 kg of permeate per m² membrane area to 5000 kg of permeate per m² membrane area has been obtained, preferably from 50 kg of permeate per m² membrane area to 1000 kg of permeate per m².

By means of the process according to the invention, a solution of glucans having a β-1,3-glycosidically linked main chain and side groups having a β-1,6-glycosidic bond thereto which is suitable for tertiary mineral oil production can be prepared in a simple manner.

The asymmetrical membranes used according to the invention are economical. Owing to the high permeate flows, the membrane plant requires low capital costs and has a low energy consumption. The asymmetrical membranes have long service lives.

The good quality of the product is evident from the good filtration properties, which are expressed by the low filtration ratio (MPFR value). The MPFR value of the product is from 1.001 to 2.5, but in particular from 1.01 to 2.0.

The yield of schizophyllan, i.e. the amount of schizophyllan which can be recovered from the fermentation discharge, based on the amount of schizophyllan present in the fermentation discharge, is from 25% to 97%, in particular from 30% to 95% and very particularly preferably from 50% to 93%.

The yield of glucan can optionally be increased by the diafiltration process using water, which is known to the person skilled in the art.

The following examples are intended to illustrate the invention in more detail:

Determination of the Filtration Ratio (MPFR Value)
Principle of Measurement:
In the determination of the Millipore filtration ratio (MPFR value), the amount of filtrate which runs through a defined filter is determined as a function of time. The MPFR value is determined according to the following formula (I)

$$\text{MPFR} = (t_{190g} - t_{170g})/(t_{70g} - t_{50g}) \qquad (I),$$

where the variables and the equation have the following meaning:
$t_{190g}$=time in which 190 g of filtrate are obtained,
$t_{170g}$=time in which 170 g of filtrate are obtained,
$t_{70g}$=time in which 70 g of filtrate are obtained,
$t_{50g}$=time in which 50 g of filtrate are obtained.

Thus, in each case the time span which is required for in each case 20 g of filtrate to flow through is determined, i.e. at a early time and at a late time in the filtration process, and the quotient is calculated from the two time spans. The larger the MPFR value, the more greatly is the filtration velocity slowed down with increasing duration of the filtration process. This indicates increasing blockage of the filter, for example by gels or particles.

The MPFR value is determined by the following method:
1. Equipment
a) Sartorius pressure filtration apparatus 16249; filter diameter 47 mm; with 200 ml digestion cylinder (Øi=41 mm)
b) Isopore membrane 1.2 μm; Ø 47 mm; No. RTTP04700
c) Balance
2. Preparation of the Glucan Solution
First, 50 g of a mixture of the glucan solution obtained from the experiments and ultrapure water is prepared, i.e. in a ratio such that the concentration of the glucan is 1.75 g/l. The mixture is stirred for 10 min and checked visually for homogeneity. If the mixture is still inhomogeneous, further stirring is effected until the mixture is homogeneous. The mixture is then made up to a total amount of 250 g with 200 g of ultrapure water. Thereafter, stirring is effected for at least 1 h for homogenization, after which the pH is adjusted to 6.0 with 0.1 M NaOH and stirring is then effected again for 15 min. The pH of 6.0 is checked again. The final concentration of the glucan in the mixture is 0.35 g/l.
3. Carrying Out the Filtration Test
The filtration test is effected at room temperature (T=25° C.) at a pressure of 1.0 bar (compressed air or $N_2$).
place coarse support grid on the sieve tray
place fine support grid on the sieve tray
place membrane filter on top
insert seal (O-ring)
screw sieve tray and outlet tap to the cylinder
close outlet tap
introduce 220 g (about 220 ml) of solution
screw upper cover to cylinder
clamp on inlet air tube
check pressure and adjust to 1.0 bar
place beaker on the balance under the filtration apparatus. Press tare.
open outlet tap
the test is stopped when no more filtrate emerges.
By means of the balance, the amount of filtrate is determined as a function of time. The mass indicated in each case can be read visually but of course also automatically and evaluated.

Retention:
The retention R is used for characterizing the separation behavior of the membrane (cf. Melin, Rautenbach, loc. cit., page 6).
R=1−(concentration of glucan in the permeate) at a time divided by the concentration of glucan in the retentate at this time.
Since the glucan is obtained as permeate, the retention should be as low as possible. In the case of a microfiltration, the retention is as a rule greater than 0%. Since the retention may change in the course of time, an average retention over the time is stated as the characteristic.

With the filter membranes used according to the invention, average retentions of less than 60%, in advantageous cases even less than 30%, are obtained. This means the glucan can be substantially recovered from the fermentation broth.

Concentration Factor:

In the concentration of the fermentation broth, the concentration factor MK is an important quantity. It is defined as the ratio of the mass of the fermentation broth used at the time zero divided by the mass of the fermentation broth at the end of the glucan isolation. The concentration factor should be as large as possible.

With the process according to the invention, concentration factors up to 15, in advantageous cases even up to 30, can be achieved.

Comparative Example

Filtration Using a Symmetrical Filter Membrane

Figure 2:
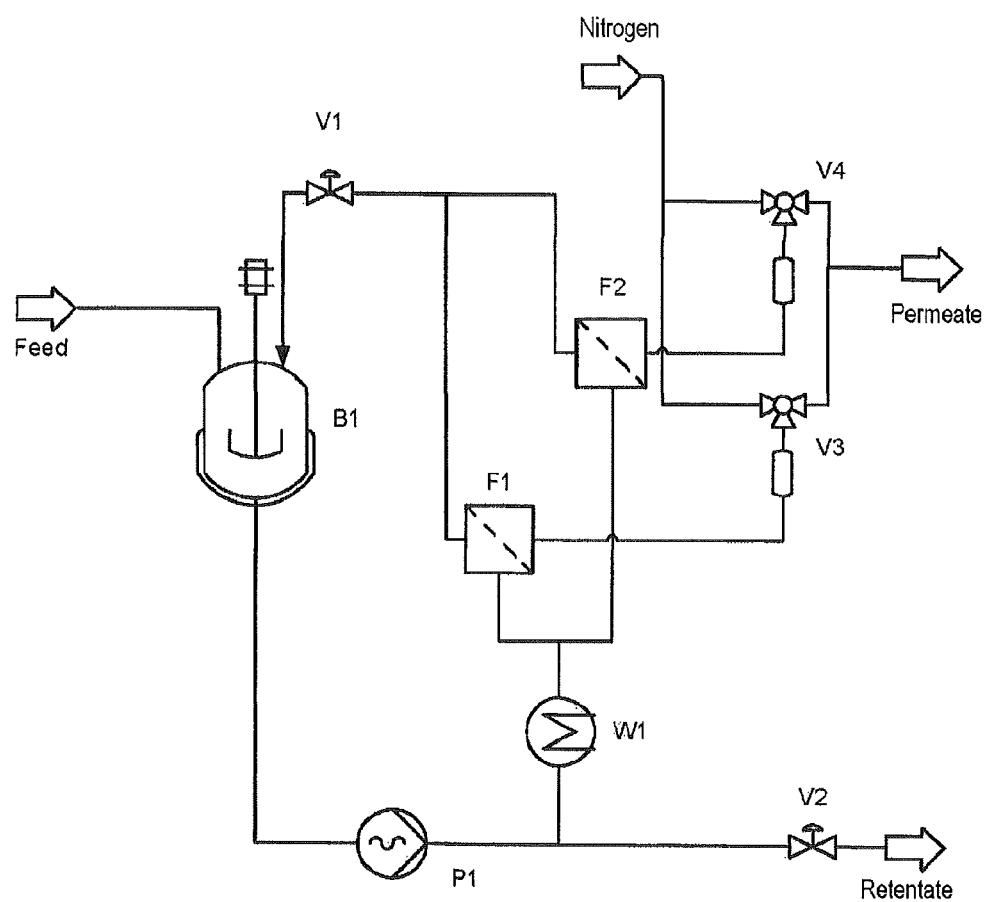
FIG. 2: schematic diagram of the apparatus used for the experiments and comparative experiments.

The crossflow filtration apparatus used is shown in FIG. 2. It consisted of a stirred double-jacket receiver B1 having a volume of 120 liters, the eccentric screw pump P1, the tube-bundle heat exchanger W1, the pressure relief valve V1 and the two filter modules F1 and F2. The filter modules F1 and F2 were back-washed with permeate by means of the three-way valves V3 and V4 at intervals of 300 s in each case with in each case 200 ml of permeate, and the pressure of nitrogen was 7 bar. The content of the crossflow filtration plant was cooled to 24° C. via the double jacket of the container B1 and the heat exchanger W1.

In the filter modules F1 and F2, a symmetrical tubular membrane was used, i.e. a 5-channel element from TAMI comprising the ceramic ATZ (alumina/titania/zirconia). The pore size D90 of the membrane was 3.5 µm. The membrane had a symmetrical structure and possessed no separating layer or intermediate layers. The length of the membrane tube was 1 m and the external diameter was 20 mm. The membrane area of a module element was 0.11 m². The hydraulic diameter of a channel was 6 mm.

*Schizophyllum commune* was used for the experiments, i.e. the schizophyllan as described in "Udo Rau, *Biopolymers*, editor A. Steinbüchel, WILEY-VCH Publishers, Volume 6, pages 63 to 79" was prepared in a batch fermentation. The fermentation time was 96 hours. 99.6 kg of this fermentation broth (=feed) was introduced into the container B1 (FIG. 2) and circulated for 45 minutes at 4 bar pressure at a circulation rate of 7 m³/h by means of the pump P1. The content of the container was analyzed and a content of 9.8 grams of schizophyllan per liter was determined.

The circulation rate was then set to 5.1 m³/h and a transmembrane pressure of 1.1 bar applied. The transmembrane flow rate was 5 m/s. The permeate emerging from the filter modules was collected and weighed. During the first 10 minutes of the experiment, 0.75 kg of permeate was obtained. This corresponds to a permeate flow of 20.4 kg/h/m2. The transmembrane pressure was 2.9 bar. The filtration was operated for 16 hours and 6.18 kg of permeate were obtained in this time. Within the last hour, it was possible to obtain only 5.4 g of permeate since the membranes were virtually completely blocked.

The permeate collected was analyzed and a glucan content of 6.7 grams per liter was found. The yield was therefore only 4%. The MPFR value of the permeate was 2.8 and the average retention of glucan during the experiment was 32%. The concentration factor was only 1.07.

Inventive Example 1

Filtration Using an Asymmetrical Filter Membrane

Once again, the crossflow filtration apparatus described in Example 1 was used. The filter modules F1 and F2 were back-washed with permeate by means of the three-way valves V3 and V4 at intervals of 120 s in each case with in each case 200 ml of permeate and the pressure of the nitrogen was 4 bar. The content of the crossflow filtration plant was cooled to 22° C. by the double jacket of the container B1 and the heat exchanger W1.

An asymmetrical tubular membrane comprising SIC was used in the filter modules F1 and F2, i.e. a 37-channel element (model "CRYSTAR, Type FT 3000" from St. Gobain). The pore size D90 of the membranes was 3.0 µm. The pore size D90 of the support material was 30 µm. The length of the membrane tube was 1 m and the external diameter was 32 mm. The membrane area of a module element was 0.42 m². The hydraulic diameter of a channel was 3.4 mm.

The fermentation discharge described in Example 1 was used for the experiments. 115 kg of this fermentation broth (=feed) were introduced into the container B1 and circulated for 50 minutes at 4 bar pressure and a circulation rate of 7 m³/h by means of the pump P1. The content of the container was analyzed and a content of 8.7 grams of schizophyllan per liter was determined.

Thereafter, the circulation rate was set to 4.1 m³/h and a transmembrane pressure of 1.1 bar was applied. The transmembrane flow velocity was 1.7 m/s. The permeate emerging from the filter modules was collected and weighed. 50 minutes after the beginning of the permeate take-off, 25 kg of fermentation broth were added to the container B1. 16 hours and 20 min after the beginning of the permeate take-off, 40 kg of fermentation broth were added to the container B1 and the circulation rate was set to 6.5 m³/h. Up to this time, 77 kg of permeate had been obtained. This corresponds to an average permeate flow of 5.6 kg/m2/h. After 20 hours since the beginning of the experiment, a further 55 kg of fermentation broth were added to the container B1. After 22.5 h after the beginning of the experiment, 109 kg of permeate had collected in the permeate container. The permeate was analyzed.

The MPFR value of the permeate in this first filtration step was 1.3. The content of schizophyllan was 6.9 grams per liter (average retention up to this time 26%) and the viscosity at 7/s was 1380 mPa·s.

The collecting container for the permeate was now changed, a further 20 kg of fermentation broth was added to the container B1 and the filtration was operated for a further 19.5 h. In this time, a further 85 kg of permeate were obtained. This corresponds to an average permeate flow of 5.1 kg/h/m2.

The permeate collected during the second filtration step was analyzed. The MPFR value was 1.2 and the content of schizophyllan was 7.8 grams per liter (average retention over the total experiment 29%) and the viscosity at 7/s was 1560 mPa·s. The yield over both filtration steps was therefore 64%. The concentration factor was 4.2.

Discussion

The values of the comparative example and of the example are listed again in Table 1 below.

TABLE 1

|  | Comparative example | Example 1 | |
| --- | --- | --- | --- |
|  |  | 1st stage | 2nd stage |
| MPFR value | 2.8 | 1.3 | 1.2 |
| Retention | 32% | 26% | 29% |
| Concentration factor | 1.07 | 4.2 |  |
| Yield | 4% | 64% |  |

The experiments show that the product filtered according to the invention comprises substantially fewer constituents which can block the 1.2 μm filter during the determination of the MPFR value. With the process according to the invention, the fermentation broth can be concentrated to a much greater extent. The yield in the process according to the invention is substantially higher and moreover the retention in the example according to the invention using asymmetrical filter membranes is substantially lower than in the comparison using symmetrical filter membranes.

Inventive Example 2

Filtration Using an Asymmetrical Filter Membrane

Once again, the crossflow filtration apparatus described in Example 1 was used.

Figure 3:
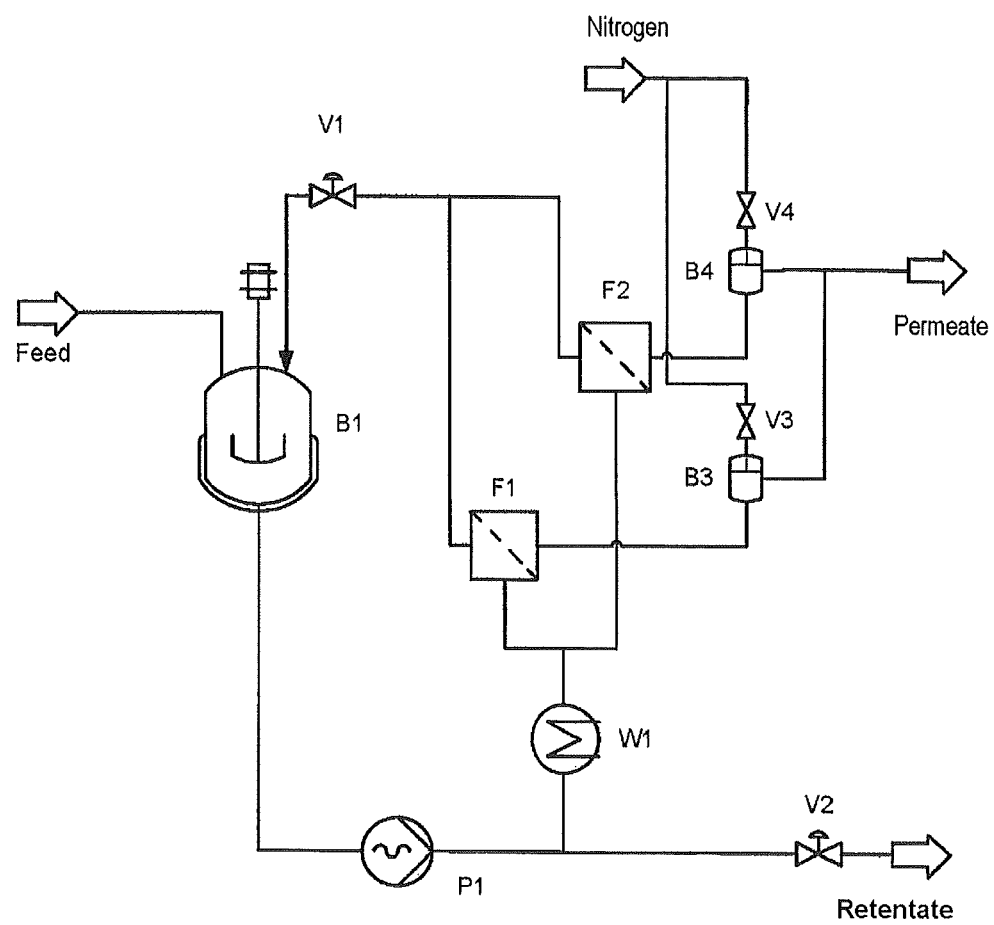
FIG. 3: schematic diagram of the apparatus equipped for permeate back-washing

However, the apparatus was equipped for permeate backwashing with two "BACKPULSE DECOLMATEUR BF 100" piston systems (see FIG. 3, positions B3 and B4). The filter modules F1 and F2 were back-washed with permeate by means of the ball valves V3 and V4 at intervals of 900 s in each case with in each case 100 ml of permeate, and the pressure of the nitrogen was 10 bar.

The double jacket surrounding the container B1 and the heat exchanger W1 were used to temperature-control the content of the crossflow filtration unit to 29° C. to 30° C.

An asymmetrical tubular membrane comprising alumina was used in the filter modules F1 and F2, i.e. a 19-channel element (model "MEMBRALOX, Type EP 1940" from Pall). The pore size D90 of the membranes was 5.0 μm. The pore size D90 of the support material was 12 μm. The length of the membrane tube was 1020 mm. The membrane tube has the shape of a hexagon with rounded-off corners, the distance between two opposite corners being 31 mm and the distance between two opposite edges being 28 mm. The membrane area of a module element was 0.24 m². The diameter of a channel was 4 mm.

The experiments were carried out with a fermentation discharge prepared as described in the comparative example and containing 8.3 grams of schizophyllan per liter. At the start of the experiments, 100 kg of this fermentation broth (=feed) were introduced into the container B1, the circulation rate of the pump P1 was set to 2.8 m³/h and a transmembrane pressure of 0.9 bar. The transmembrane flow velocity was 1.6 m/s. The permeate emerging from the filter modules was collected and weighed. 20 minutes after the beginning of the permeate take-off, 41 kg of fermentation broth were added to the container B1. 10 hours and 35 min after the beginning of the permeate take-off, the transmembrane pressure had risen to 1.8 bar. The permeate take-off was interrupted. Up to this time, 100.6 kg of permeate had been obtained. This corresponds to an average permeate flow of 19.8 kg/m²/h. The permeate was analyzed. The MPFR value of the permeate in this first filtration step was 1.7. The content of schizophyllan was 6.3 grams per liter.

The collecting container for the permeate was now changed, a further 107 kg of fermentation broth were added to the container B1 and the transmembrane pressure was set to 1.2 bar. After 7 hours 55 minutes from the beginning of this second filtration step 24.3 kg of permeate were recovered. This corresponds to an average permeate flow of 6.4 kg/m²/h. The analysis of the permeate in this first filtration step gave an MPFR value of 1.6 and a content of schizophyllan of 7.4 grams per liter.

The collecting container for the permeate was now changed and the filtration operated for a further 15 hours. In this time, a further 47.2 kg of permeate were obtained, the transmembrane pressure rose to 1.5 bar. The average permeate flow was 6.6 kg/h/m². The permeate collected during the third filtration step was analyzed. The MPFR value was 2.2, the content of schizophyllan was 7.7 grams per liter.

The yield of glucan over the three filtration steps was 57%, the concentration factor was 3.3 and the retention was 28%.

The invention claimed is:

1. A process for the preparation of aqueous solutions of glucans having a β-1,3-glycosidically linked main chain and side groups having a β-1,6-glycosidic bond thereto, comprising:
    a) fermenting fungal strains which secrete said glucans in an aqueous culture medium; and
    b) subsequently separating an aqueous solution of the resulting glucan from the aqueous fermentation broth comprising glucans and biomass by crossflow microfiltration, wherein
        (i) asymmetrical filter membranes comprising at least one layer of a support material and at least one separating layer are used for the crossflow microfiltration,
        (ii) the pore size of the separating layer being from 1 μm to 10 μm and the pore size of the support material being from 5 μm to 100 μm, with the proviso that the pore size of the support material is at least 1 μm greater than the pore size of the separating layer, and
        (iii) the flow velocity of the crossflow is from 0.2 m/s to 20 m/s, and
        (iv) the transmembrane pressure is from 1 to 10 bar; and
    c) wherein the concentration of the glucans in the fermentation broth to be filtered is at least 3 g/l.

2. The process of claim 1, wherein the pore size of the support material is at least 5 μm greater than the pore size of the separating layer.

3. The process of claim 1, wherein the fermentation is carried out at a temperature of from 15 to 40° C. with aeration and movement.

4. The process of claim 1, wherein the fungal strains are *Schizophyllum commune* or *Sclerotium rolfsii*.

5. The process of claim 1, wherein the asymmetrical filter membranes are ceramic.

6. The process of claim 1, wherein the asymmetrical filter membranes are metallic.

7. The process of claim 1, wherein the asymmetrical filter membranes are multichannel elements.

8. The process of claim 1, further comprising regularly backwashing the asymmetrical filter membranes.

9. The process of claim 1, wherein the fermentation is carried out in a plant comprising at least one fermentation container, fermentation broth comprising biomass and glucan is removed from the plant via a side stream, an aqueous solution of glucans is separated off therefrom by means of crossflow microfiltration, at least part of the remaining fermentation broth comprising biomass being recycled to the fermentation container.

10. The process of claim 1, further comprising regularly cleaning the asymmetrical filter membranes with a mixture of hydrogen peroxide and alkali, with the proviso that the cleaning is effected in each case as soon as an amount of from 50 kg of permeate per $m^2$ membrane area to 5000 kg of permeate per $m^2$ membrane area has been reached after a preceding cleaning.

11. The process of claim 1, further comprising regularly cleaning the asymmetrical filter membranes with a mixture of hypochlorite and alkali, with the proviso that the cleaning is effected in each case as soon as an amount of from 50 kg of permeate per $m^2$ membrane area to 5000 kg of permeate per $m^2$ membrane area has been reached after a preceding cleaning.

* * * * *